US011460393B2

(12) United States Patent
Kent et al.

(10) Patent No.: US 11,460,393 B2
(45) Date of Patent: Oct. 4, 2022

(54) SYSTEM AND METHOD FOR ACCELERATED WEATHERING TESTING OF INSULATING GLASS UNITS

(71) Applicant: The Insulating Glass Certification Council, Sackets Harbor, NY (US)

(72) Inventors: John Grant Kent, Henderson Harbor, NY (US); Steve E. Yerden, Redfield, NY (US); Mitchell Paul Majewski, Sandy Creek, NY (US)

(73) Assignee: The Insulating Glass Certification Council, Sackets Harbor, NY (US)

( * ) Notice: Subject to any disclaimer, the term of this patent is extended or adjusted under 35 U.S.C. 154(b) by 170 days.

(21) Appl. No.: 16/896,469

(22) Filed: Jun. 9, 2020

(65) Prior Publication Data

US 2020/0408668 A1 Dec. 31, 2020

Related U.S. Application Data

(60) Provisional application No. 62/867,395, filed on Jun. 27, 2019.

(51) Int. Cl.
*G01N 17/00* (2006.01)
*G01N 33/38* (2006.01)

(52) U.S. Cl.
CPC ......... *G01N 17/002* (2013.01); *G01N 33/386* (2013.01)

(58) Field of Classification Search
CPC .... G01N 17/004; G01N 17/002; G01N 17/02; G01N 17/006

(Continued)

(56) References Cited

U.S. PATENT DOCUMENTS 1,558,786 A * 10/1925 Buttolph .............. G01N 17/004
                                                   73/150 R
3,664,188 A * 5/1972 Kockott ............... G01N 17/004
                                                   73/150 R (Continued)

FOREIGN PATENT DOCUMENTS

CN      103781645 A * 5/2014 ............ B60J 7/0015
CN      107300938 A * 10/2017

(Continued)

OTHER PUBLICATIONS

ESPACENET Machine Translation of CN 107300938 A Which Originally Published On Oct. 27, 2017. (Year: 2017).*

(Continued)

*Primary Examiner* — David A. Rogers
(74) *Attorney, Agent, or Firm* — Knobbe Martens Olson & Bear, LLP

(57) ABSTRACT

An accelerated weathering device, system and method is provided for rapidly weather testing insulating glass units (IGUs). The accelerated weathering system can include an air sealed vessel that can removably house an IGU, an air flow system in fluid communication with a chamber in the vessel, the air flow system operable to increase or decrease a pressure in the chamber, an exchanger system in communication with the chamber and operable to increase or decrease one or both of a temperature and a humidity level of the chamber, one or more UV bulbs, and a computer system operable to control the air flow system and exchanger system to vary one or more of the following parameters in the chamber: temperature, relative humidity, and pressure.

6 Claims, 8 Drawing Sheets

(58) Field of Classification Search
USPC .......................................................... 73/865.6
See application file for complete search history.

(56) References Cited

U.S. PATENT DOCUMENTS

| | | | | |
|---|---|---|---|---|
| 3,686,940 A * | 8/1972 | Kockott | ............... | G01N 17/004 359/359 |
| 3,693,020 A * | 9/1972 | Ackerman, Jr. | ..... | G01N 17/004 250/372 |
| 3,886,791 A * | 6/1975 | Grossman | ............... | G01N 17/00 73/150 R |
| 4,011,456 A * | 3/1977 | Bredewater | ............ | B01J 19/123 250/492.1 |
| 4,131,588 A * | 12/1978 | Smith, Jr. | ................. | C08K 3/34 524/789 |
| 4,391,522 A * | 7/1983 | Schmid et al. | ........ | G01J 3/0237 73/150 R |
| 4,627,287 A * | 12/1986 | Suga | ..................... | G01N 17/004 73/159 |
| 4,747,645 A * | 5/1988 | Rudzki | ................ | G01N 17/004 250/492.1 |
| 4,760,748 A * | 8/1988 | Katayanagi | .......... | G01N 17/004 374/57 |
| 4,770,542 A * | 9/1988 | Takagi | .................... | B29C 71/04 374/57 |
| 4,817,447 A * | 4/1989 | Kashima | ................ | G01N 17/00 374/57 |
| 4,874,952 A * | 10/1989 | Arnaud | ................ | G01N 17/004 250/455.11 |
| 4,886,095 A * | 12/1989 | Lisec | ....................... | E06B 3/677 141/4 |
| 5,660,794 A * | 8/1997 | Gilbreath, Jr. | ........ | G01N 17/004 250/492.1 |
| 5,898,816 A * | 4/1999 | Heeger | ................ | G01N 17/004 392/408 |
| 6,626,052 B1 * | 9/2003 | Martin | ................... | G01N 17/004 250/228 |
| 7,013,742 B2 * | 3/2006 | Beraud | ................ | G01N 17/004 250/492.1 |
| 7,124,651 B2 * | 10/2006 | Ketola | ................. | G01N 17/004 73/865.6 |
| 7,258,757 B2 * | 8/2007 | Huang | ............. | B32B 17/10009 156/107 |
| 7,348,581 B2 * | 3/2008 | March | .................. | G01N 17/004 250/504 R |
| 7,353,722 B2 * | 4/2008 | Schonlein | ............. | G01N 17/00 250/492.1 |
| 7,454,990 B2 * | 11/2008 | Hardcastle, III | ..... | G01N 17/004 250/492.1 |
| 8,225,682 B2 * | 7/2012 | Schultz | ................ | G01N 17/004 73/865.6 |
| 9,063,050 B2 * | 6/2015 | Suga | ..................... | G01N 17/004 |
| 9,250,224 B2 * | 2/2016 | Byun | ...................... | G01N 17/00 |
| 9,267,875 B2 * | 2/2016 | Yap | ........................ | H01L 21/67 |
| 9,377,391 B2 * | 6/2016 | Schoenlein | .......... | G01N 17/002 |
| 9,459,185 B2 * | 10/2016 | Thompson | ......... | G01N 33/0016 |
| 9,528,927 B2 * | 12/2016 | Rudolph | ............. | G01N 17/002 |
| 9,733,224 B2 * | 8/2017 | Thompson | ......... | G01N 33/0016 |
| 10,620,113 B2 * | 4/2020 | Yoshida | ............... | G01N 17/002 |
| 10,627,359 B2 * | 4/2020 | Haglin | .................. | G01N 27/18 |
| 11,016,029 B2 * | 5/2021 | Yin | ........................ | G01N 21/76 |
| 2002/0192371 A1 * | 12/2002 | Veerasamy | .......... | C03C 17/3655 427/249.7 |
| 2006/0037412 A1 * | 2/2006 | Brunner | ............... | G01N 17/002 73/865.6 |
| 2006/0090834 A1 * | 5/2006 | Huang | ................... | B32B 27/36 156/99 |
| 2007/0034026 A1 * | 2/2007 | Maciver | ............... | G01N 17/002 73/865.6 |
| 2009/0314107 A1 * | 12/2009 | Yakimoski | ........... | G01N 17/002 73/865.6 |
| 2016/0131571 A1 * | 5/2016 | Yap | ......................... | H01L 21/67 73/865.6 |
| 2016/0187247 A1 * | 6/2016 | Rey | ........................ | G01N 25/72 374/57 |
| 2018/0100823 A1 * | 4/2018 | Haglin | ................... | G01N 27/18 |
| 2019/0011352 A1 * | 1/2019 | Yoshida | ............... | G01N 17/002 |

FOREIGN PATENT DOCUMENTS

| | | | | |
|---|---|---|---|---|
| CN | 105482575 B | * | 11/2017 | |
| CN | 107044953 B | * | 1/2018 | |
| CN | 108956444 A | * | 12/2018 | |
| CN | 112557288 A | * | 3/2021 | .......... G01N 17/004 |
| EP | 2341490 A1 | * | 7/2011 | ............. G08B 13/04 |
| EP | 2943771 B1 | * | 9/2019 | .......... G01N 17/004 |
| FR | 2983581 A1 | * | 6/2013 | ............. G01M 7/02 |
| JP | 61038446 A | * | 2/1986 | |
| JP | H0778594 A | * | 1/1995 | |
| KR | 20130084333 A | * | 7/2013 | .......... G01N 17/004 |
| WO | WO-9749779 A1 | * | 12/1997 | ............... C09K 3/10 |
| WO | WO-2010000082 A1 | * | 1/2010 | ............... G08B 3/10 |

OTHER PUBLICATIONS

"Standard Test Method for Accelerated Weathering of Sealed Insulating Glass Units, E773-97", American Society for Testing Materials, 1997. (Year: 1997).*

Guide to Weather Performance Testing of Windows & Doors, British Woodworking Federation, 2017. (Year: 2017).*

* cited by examiner

FIG. 9

SYSTEM AND METHOD FOR ACCELERATED WEATHERING TESTING OF INSULATING GLASS UNITS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The invention is directed to a system and method for testing products, such as insulating glass units, and more particularly to a system and method for accelerated weathering testing of products (e.g., insulating glass units) to assess their quality and estimate their long-term durability.

Description of the Related Art

Numerous accelerated weathering devices have been developed or proposed over the years for products with an extended life expectancy, where real-life lifespan data takes too long to develop. These apparatuses are intended to help predict the long-term performance of manufactured products or assemblies when exposed to various stressful environments that are known to cause degradation over time. Accelerated weathering devices typically increase the intensity of the test environments of the in-service real-life environment conditions and/or decrease any cycle time periods. The stressful environments can include: direct tensile and bending stresses, high and low temperatures, low and high humidity, specific wavelength electromagnetic radiation, usually ultra-violet wavelengths, and elevated and reduced air pressures. Stressful environments can be either sustained or cyclical. For example, relatively static air pressure has been used in laboratory tests to simulate wind loads and atmospheric pressure loads.

Previous accelerated weathering devices had several drawbacks. For example, in these devices, most of which were non-closed systems, the required degree of precision for the chamber environments, which included high temperatures, high moisture content, high and low air pressures, and non-uniform ultra-violet exposure, did not reach an acceptable level. The lack of precision was primarily caused by the significant quantity of air movement required to rapidly cycle the air pressure, along with the lack of precision of the physical properties of the chamber environment. These issues rendered such accelerated weathering devices of little practical value.

Products with air-tight seals, and those that are relatively large, such as insulating glass units, present additional difficulties as in-service environments such as impacts, wind-loads, temperature changes, and atmospheric pressure changes can induce additional stresses into the seals and product components.

The current insulating glass unit industry test methods (ASTM E-2188 & E-2190) and its test devices have several significant problems. For example, the tests take a long time to complete—e.g., up to six months (22-24 weeks) or more—as it uses a four to six-hour temperature cycle rate. Additionally, the test chambers are expensive to build and operate. Still another drawback of existing test methods and devices is that the operation of the current chambers is complicated and difficult. Another problem is that there is substantial variability in the chamber conditions. Still another drawback is that the test units must be handled multiple times to place them in multiple testing chambers. Another problem is that there is little opportunity for fabricators and suppliers to use the current testing method to perform their own Quality Assurance, or correlate to laboratory results.

The current test specifications for insulating glass units are based upon 50 years of "field" experience. However, as the length of time to carry out a single test increases, the number of tests needed for calibration purposes increases, and the imprecision of the method increases, the existing test systems and methods cannot be confidently modified without a more rapid way to accurately evaluate the effectiveness of any changes.

SUMMARY

In accordance with one aspect of the disclosure, an accelerated weathering device, system and method is provided for rapidly and conveniently weather testing products (e.g., in approximately 2-3 weeks). Such products may include an air-tight seal.

In accordance with another aspect of the disclosure, an accelerated weathering device, system and method is provided for rapidly weather testing insulating glass units, which include a long and exposed peripheral air-tight seal and have an expected life of several decades.

In accordance with another aspect of the disclosure, a calibration method is provided to readily compare a particular test specification degradation rate to other test specifications and to a real-world degradation rate for the seals of insulating glass units (IGUs). The degradation rate is established by the time-related conditions of the gas sealed inside the test samples and installed products.

In accordance with another aspect of the disclosure, in one implementation the accelerated weathering device, system and method uses rapid cycling of air pressure (e.g., every minute) to simulate stresses on or in the test samples due to wind, atmospheric changes, and/or the effects of temperature on air sealed assemblies.

In accordance with another aspect of the disclosure, in one implementation the accelerated weathering device, system and method exposes the test samples (e.g., IGUs) to ultraviolet light radiation (e.g., in cycles) to simulate the effect of UV radiation on the test samples.

In accordance with another aspect of the disclosure, in one implementation the accelerated weathering device, system and method exposes the test samples (e.g., IGUs) to cycles in humidity to simulate the effect of different temperatures and humidity levels on the test samples.

BRIEF DESCRIPTION OF THE DRAWINGS

FIG. 9 is a time-chart illustrating the measured environmental conditions within the chamber along with the gas sealed within each of six insulating glass unit test samples, which provides data related to the durability performance of the samples' air-tight seals.

DETAILED DESCRIPTION

Figure 1:
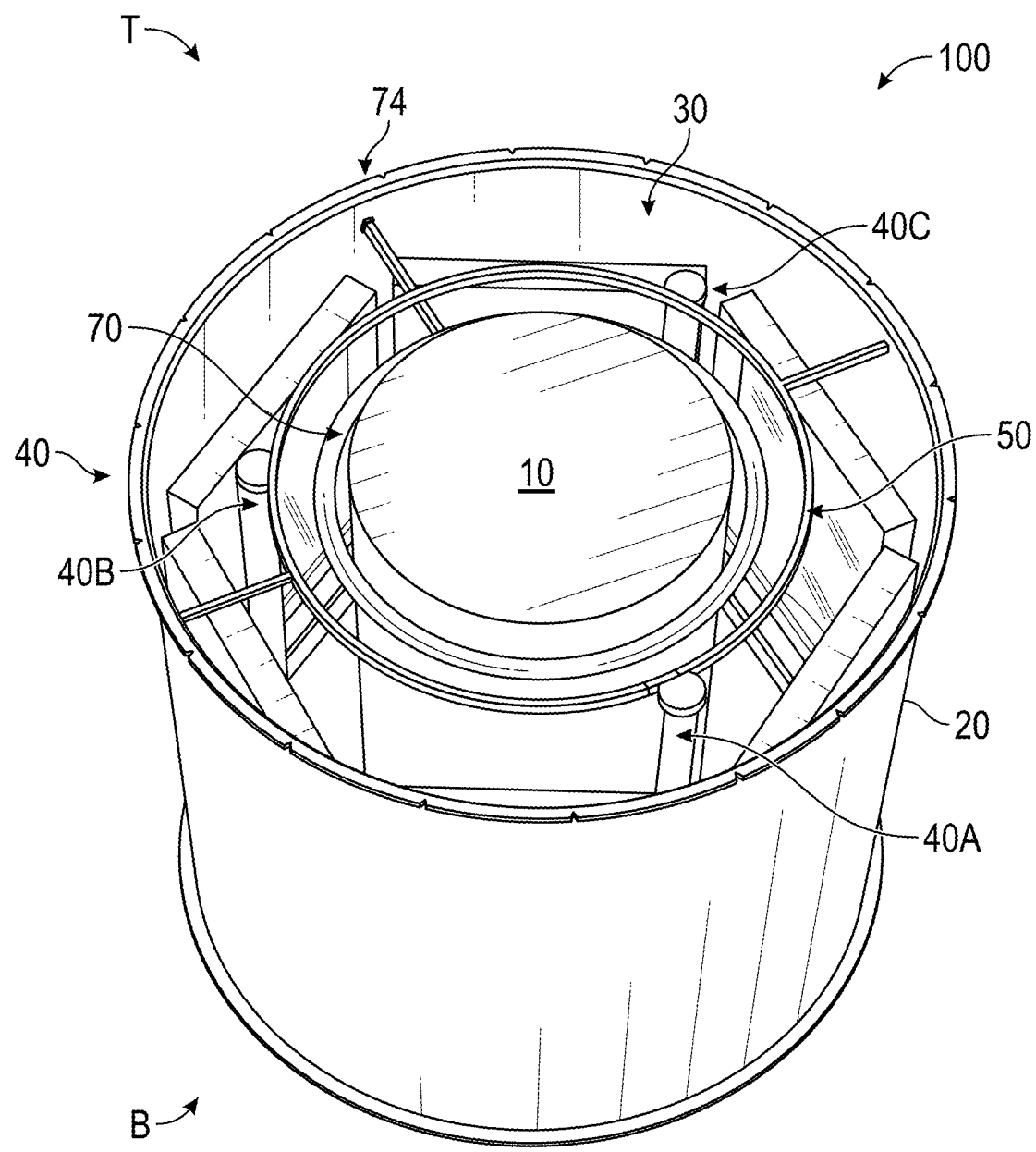
FIG. 1 is a top and side perspective view of a test chamber vessel.

FIGS. 1-5 show a test chamber vessel 100 (the "vessel") for use in weather testing of one or more test samples 600 placed in the vessel 100. The one or more test samples 600 can be six test samples 600, though the number can be higher or lower. The test samples 600 can optionally be insulating glass units (IGUs), each having an air-tight seal. However, in other implementations, the test samples 600 can be other products (e.g., having an air-tight seal) that are exposed to different environmental conditions in use (e.g., different humidity levels, different temperatures, different pressures, different ultraviolet radiation levels, etc.).

The vessel 100 can have a post or cooling tower 10 (e.g., linear post, cylindrical post) and a wall 20 (e.g., peripheral wall, cylindrical wall) that is spaced about the post 10 to define an annular gap or space 30 therebetween. The outer wall 20 can extend from a bottom B of the vessel 100 to a top T of the vessel 100. The post 10 can extend from the bottom B of the vessel upward toward the top T of the vessel 100. Though not shown, the top T of the vessel 100 can be sealed (e.g., with a cover, not shown) to fully enclose the test sample(s) 600 in the vessel 100.

The test sample(s) 600 can be removably inserted into the annular gap 30. In the implementation shown in FIGS. 1-5, six test samples 600A-600F are inserted into the annular gap 30. Optionally, the test sample(s) 600A-600F are supported by corresponding pairs of brackets 60 (e.g., 60A-60F), where the test sample(s) 600A-600F are each inserted between a corresponding pair of brackets 60 that maintain the test sample(s) 600 in a substantially fixed orientation (e.g., a vertical orientation) and inhibit (e.g., prevent) movement or shifting of the test sample 600 during the test process.

The vessel 100 has one or more (e.g., multiple) ultraviolet (UV) radiation lamps 40 in the annular gap 30, each UV lamp 40 disposed near or proximate an edge of two adjacent test samples 600. In the implementation shown in FIGS. 1-5, three UV lamps 40A, 40B, 40C are provided, each being proximate adjacent edges of adjacent test samples 600. The UV lamps 40 are operable to direct UV light onto the test samples 600, as further discussed below, to expose them to UV radiation. A frame 50 that is disposed about the post 10 couples to a top portion of the UV lamps 40 to maintain them substantially in place (e.g., inhibit them from moving) within the annular gap 30. The frame 50 can couple to the wall 20.

Figure 2:
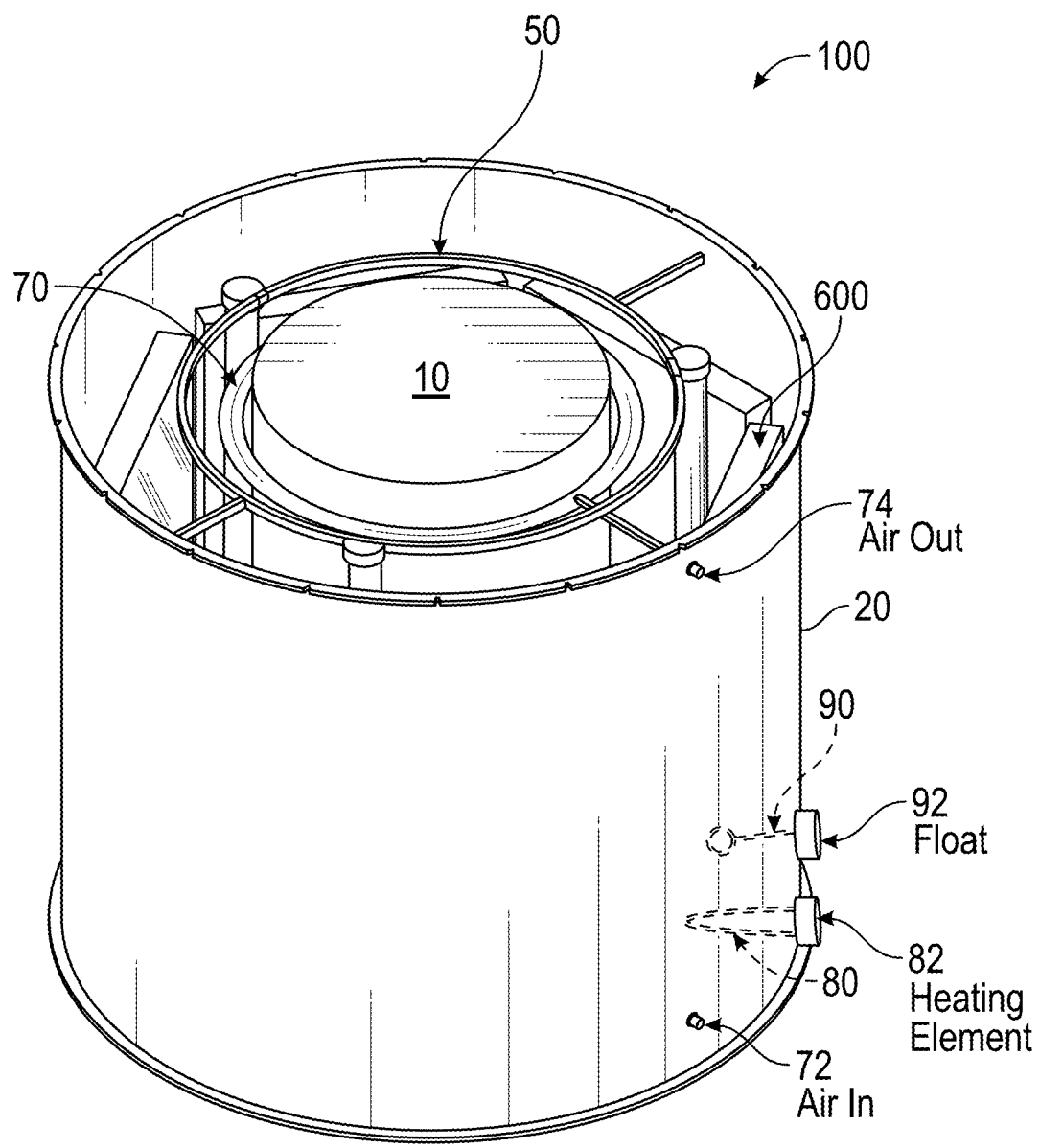
FIG. 2 is another top and side perspective view of the test chamber vessel in FIG. 1.
Figure 3:
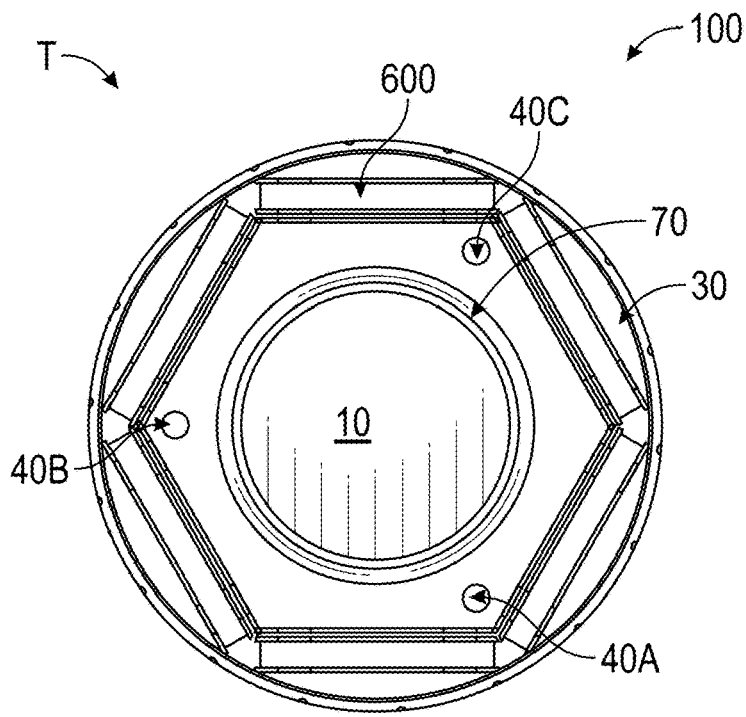
FIG. 3 is a top planar view of the test chamber vessel in FIG. 1.

With reference to FIG. 2, the vessel 100 has an air inlet port 72 and an outlet port 74 on the wall 20 via which air can be circulated into and out of the annular gap 30. The outlet port 74 can connect to an plenum or header 70 (e.g., an annular plenum disposed about the post 10) that is itself in fluid communication (e.g., via openings in the plenum or header 70) with the annular gap 30. The vessel 100 also has a heating element 80 that extends into the annular gap 30 from a connector 82 (e.g., electrical connector) on the wall 20. The heating element 80 can be operated to vary a temperature in the vessel 100 (e.g., of the annular gap 30) as further discussed below. The vessel 100 also has a float 90 that extends into the annular gap 30 from a connector or support 92 on the wall 20. The float 90 can be operated to define a liquid level during humidity testing, as further discussed below.

Figure 4:
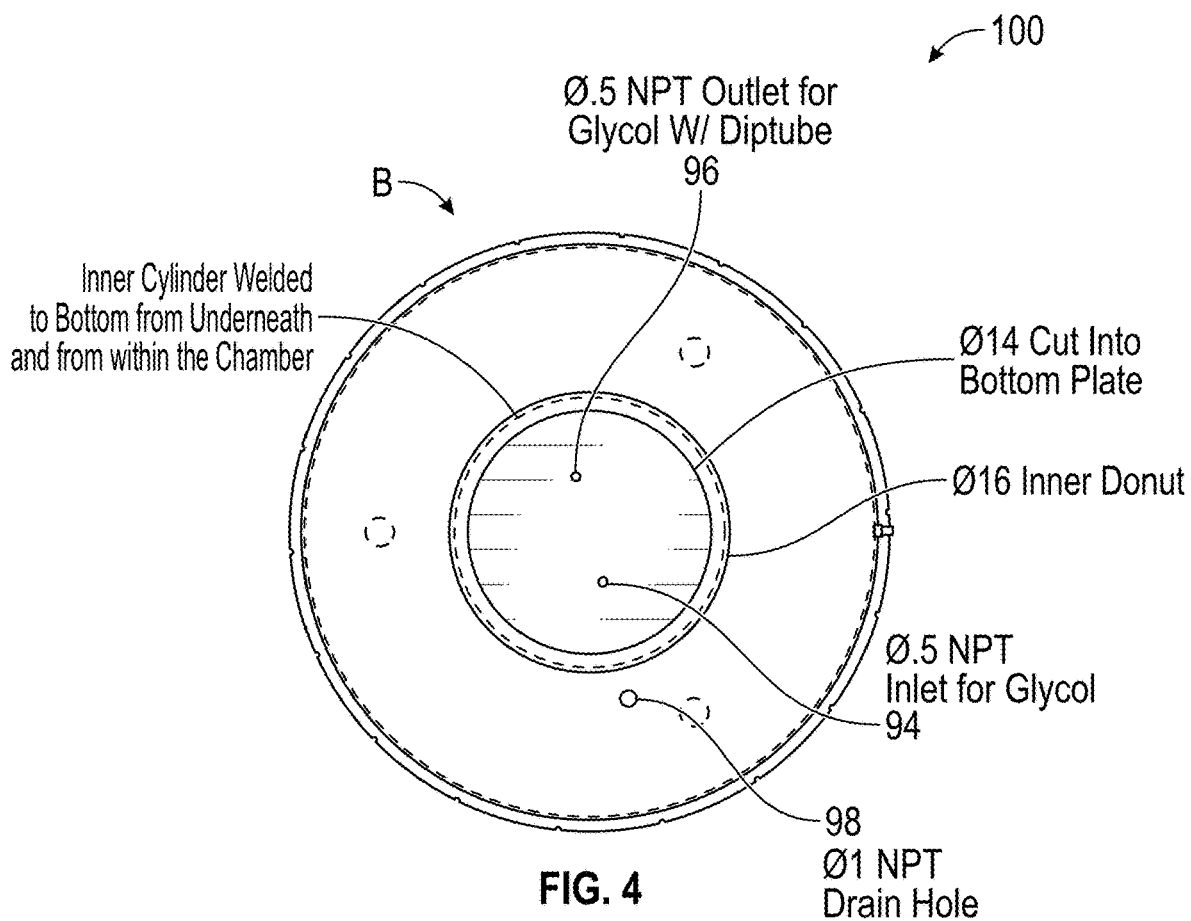
FIG. 4 is a bottom planar view of the test chamber vessel in FIG. 1.
Figure 5:
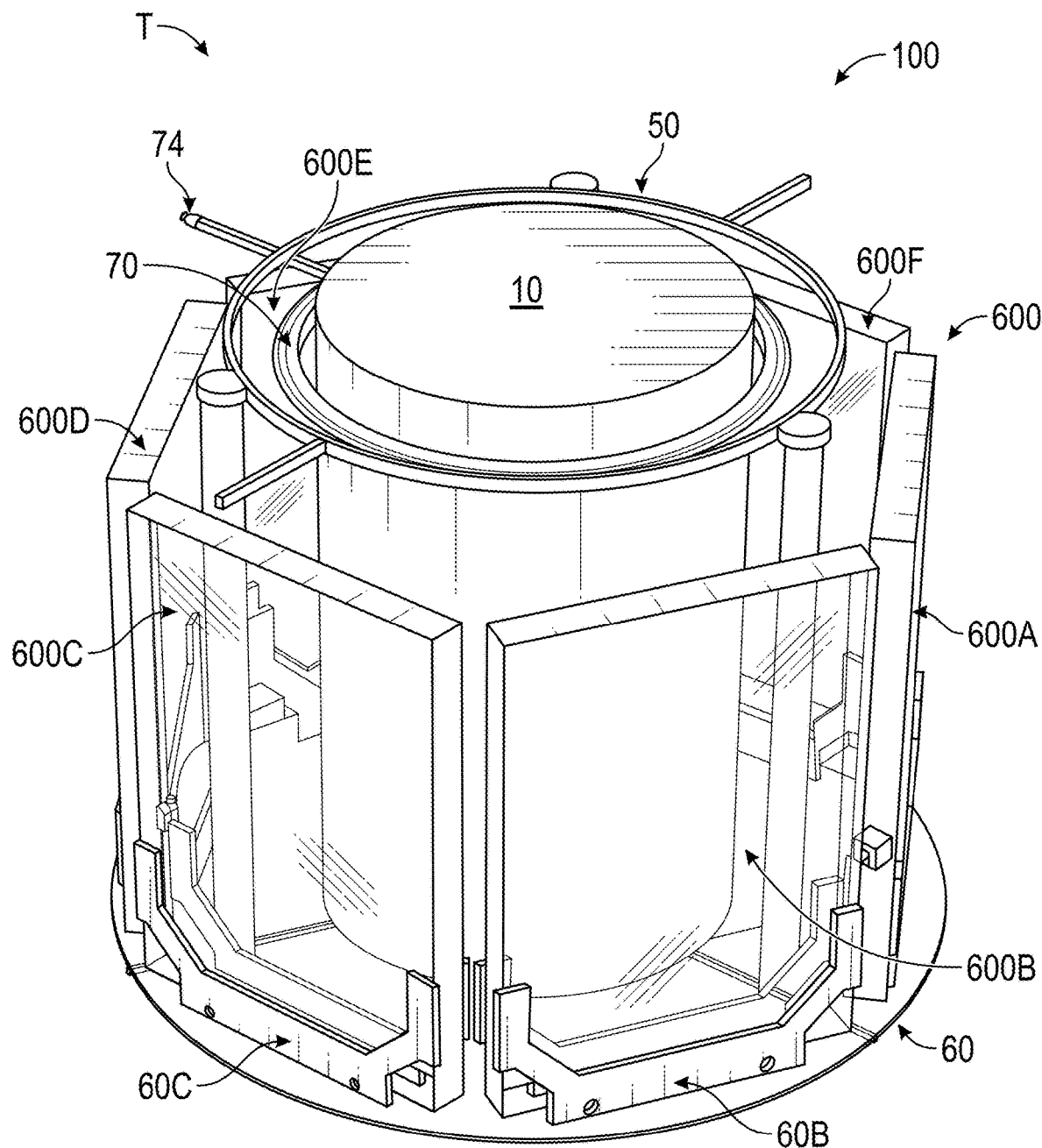
FIG. 5 is top and side perspective view of the test chamber vessel in FIG. 1 without the outer housing.

With reference to FIG. 4, the bottom B of the vessel 100 can have an inlet port 94 and outlet port 96 for intake and exhaust, respectively, of a coolant (e.g., Glycol). In another implementation, the inlet port 94 and/or outlet port 96 can be located in another suitable location. The inlet and outlet ports 94, 96 are in fluid communication with an internal volume in the post 10. The vessel 100 also includes a drain hole 98 that is in fluid communication with the annular gap 30. In one implementation, the drain hole 98 can operate as a liquid inlet and outlet, and be coupled to one or more valves that operate to delivery liquid into and remove liquid from the annular gap 30, as further discussed below. In another implementation, the drain hole 96 operates to only remove liquid from the annular gap 30, and liquid can be delivered to the annular gap 30 in another manner (e.g., via a separate port on the bottom B of the vessel, via a port in the wall 20, etc.).

Figure 6:
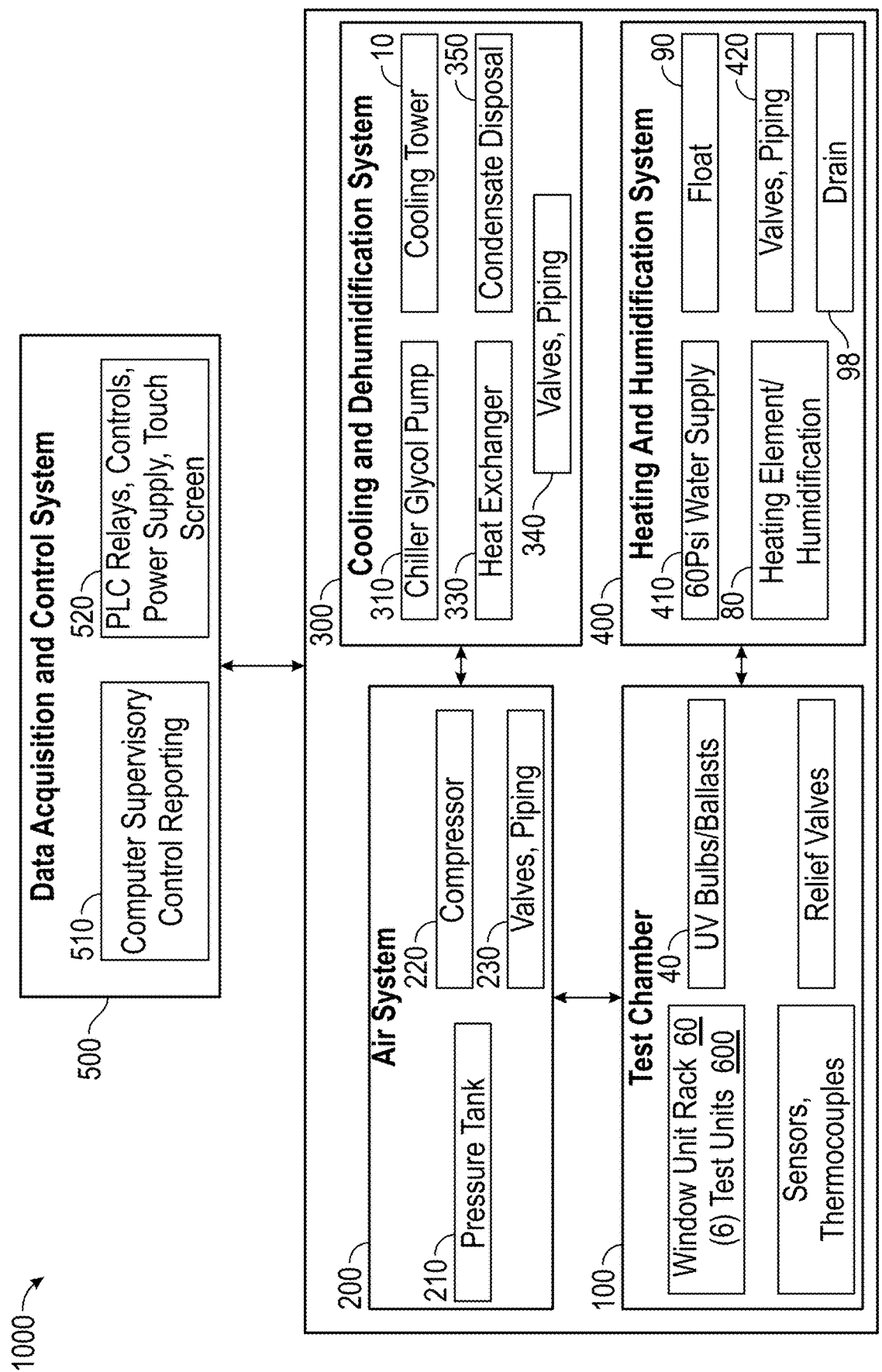
FIG. 6 is a block diagram of the accelerated weathering test system.

FIG. 6 shows an implementation of a test system 1000 that utilizes the test chamber vessel 100 for weathering testing of the test sample(s) 600. The system 1000 can optionally have one or more of (e.g., can have each of) an air system 200, a cooling and dehumidification system 300, a heating and humidification system 400 and a data acquisition and control system 500 that communicates with the vessel 100 (e.g., with the annular gap 30).

The air system 200 is operable to deliver air into the vessel 100 (e.g., via the inlet port 72 and removed via the outlet port 74). The air system 200 can optionally have a pressure tank 210, a compressor 220 and/or valves and piping 230 for delivering air to and/or removing air from the vessel 100. In operation, to increase pressure in the vessel, the air system 200 can deliver air (e.g., from the pressure tank and via the compressor) into the vessel 100. To decrease pressure in the vessel 100, or to subject the vessel 100 (e.g., annular gap 30) to a negative pressure or vacuum, the air system 200 can remove air from the vessel 100 (e.g., via the outlet port 74) and direct it to the pressure tank 210 for storage.

The cooling and dehumidification system 300 can optionally include a chiller coolant pump 310 (e.g., a Glycol pump), a cooling tower 10, a heat exchanger 330, piping and valves 340 and/or a condensate disposal 350. The cooling and dehumidification system 300 is operable to cool and/or dehumidify (e.g., decrease a humidity of) at least a portion of the vessel 100 (e.g., the annular gap 30) to expose the test sample(s) 600 to a decreased (e.g., cooler) temperature or less humid environment. For example, the system 300 is operable to deliver coolant (e.g., Glycol) in a cooled state (e.g., via the heat exchanger 330) into the vessel 100 (e.g., via the inlet port 94) to cool and/or dehumidify at least a portion of the vessel 100 (e.g., the annular gap 30). In one implementation, the coolant is delivered into a volume inside the post 100, which allows the surface of the post or cooling tower 10 to cool the air in the annular gap 30 and reduce the humidity of the air in the annular gap 30. The coolant (e.g., Glycol) can be removed from the vessel 100

(e.g. from the volume in the post or cooling tower 10) via the outlet port 96 and optionally returned to a chiller storage tank.

The heating and humidification system 400 can optionally include a water supply 410, the float 90, the heating element 80, valves and piping 420 and/or the drain 98. The heating and humidification system 400 is operable to heat and/or humidify (e.g., increase a humidity of) at least a portion of the vessel (e.g., the annular gap 30) to expose the test sample(s) 600 to an increased temperature and/or a more humid environment. For example, the system 400 is operable to deliver an amount of liquid (e.g., water) into the vessel 100 (e.g., into the annular gap 30). Optionally, water is delivered into the annular gap 30 to a level defined by the float 90. The heating element 80 can be operated to heat the water in the annular gap 30 to generate steam in the vessel 100 (e.g., in the annular gap 30) to thereby increase the temperature and/or humidity in the vessel 100 (e.g. in the annular gap 30) that the test sample(s) are exposed to. To decrease (or to stop increasing the temperature and/or humidity) in the vessel 100 (e.g., in the annular gap 30), the water can be drained via the drain 98 from the vessel 100 and power to the heating element 80 discontinued (e.g., via the power connector 82).

As shown in FIG. 6, the air system 200 can communicate with the cooling and humidification system 300 and can communicate with the test chamber vessel 100. The heating and humidification system 400 can also communicate with the test chamber vessel 100. The data acquisition and control system 500 can include a computer 510 and a PLC 520 (e.g., programmable logic controller). The system 500 can communicate with one or more of the air system 200, cooling and dehumidification system 300, test chamber vessel 100 and heating and humidification system 400. For example, the system 500 can turn on or turn off or otherwise control the operation of the systems 200, 300, 400, as well as components in the vessel 100 (e.g., the UV lamps 40, sensors and thermocouples in the vessel 100, pressure relief valves, etc.). The system 500 can collect and/or store data (e.g., pressure, temperature, humidity, UV radiation) from one or more sensors in the vessel 100, and can also generate one or more reports with the collected data.

Figure 7:
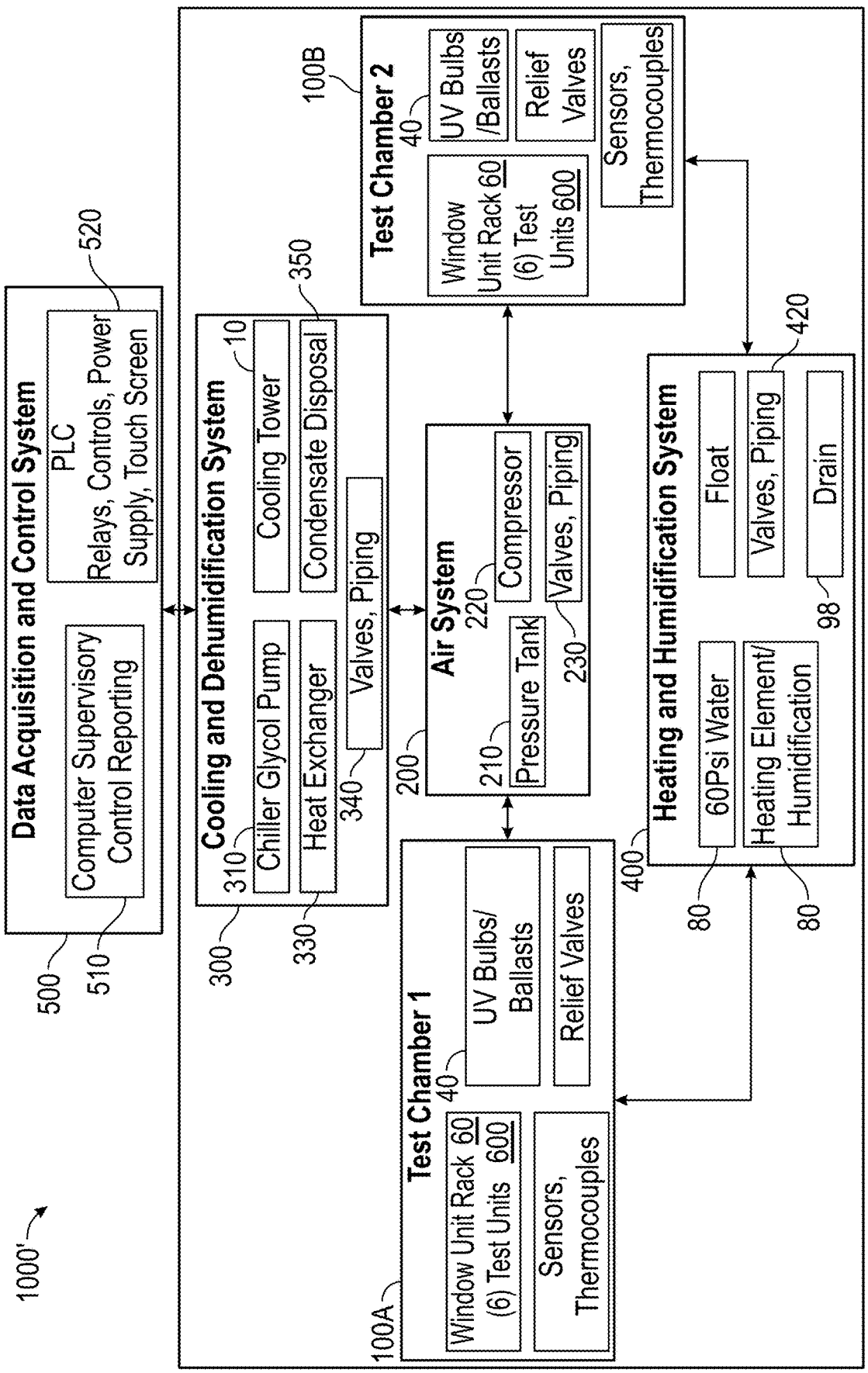
FIG. 7 is a block diagram of the accelerated weathering test system having multiple test chambers (e.g., a multi-chamber test unit).

FIG. 7 shows an implementation of a test system 1000' can optionally have one or more of (e.g., can have each of) an air system 200, a cooling and dehumidification system 300, a heating and humidification system 400 and a data acquisition and control system 500. Some of the features of the test system 1000' are similar to features of the test system 1000 in FIG. 6. Thus, references numerals used to designate the various components of the test system 1000' are identical to those used for identifying the corresponding components of the test system 1000 in FIG. 6, except that a "'" has been added to the numerical identifier. Therefore, the structure and description for the various features of the test system 1000 in FIG. 6 are understood to also apply to the corresponding features of the test system 1000' in FIG. 7, except as described below.

The test system 1000' differs from the test system 1000 in that two test chamber vessels 100A, 100B are provided instead of a single test chamber vessel 100 in FIG. 6. each of the vessels 100A, 100B can in one implementation be identical to the test chamber vessel 100 in FIGS. 1-6. Using multiple test chambers (e.g., test vessel 100A, 100B) advantageously allows for an increased number of test sample(s) to be tested at one time. As shown in FIG. 7, the air system 200 and heating and humidification system 400 are each in communication with both vessels 100A, 100B. Additionally, the cooling and dehumidification system 300 is in communication with the air system 200, and the data acquisition and control system 500 is in communication with one or more of the air system 200, cooling and dehumidification system 300, test chamber vessels 100A, 100B and heating and humidification system 400.

Optionally, the test chamber vessels 100A, 100B are operated at the same time, and one or more of the air system 200, heating and humidification system 400 and cooling and dehumidification system 300 expose the test sample(s) 600 in the vessels 100A, 100B to alternating environments. For example, the air system 200 can increase pressure in the vessel 100A while simultaneously decreasing pressure (e.g., applying negative pressure or vacuum) to the vessel 100B. In another example, the heating and humidification system 400 can alternatively or additionally increase temperature and/or humidity in vessel 100A but not in vessel 100B.

Figure 8:
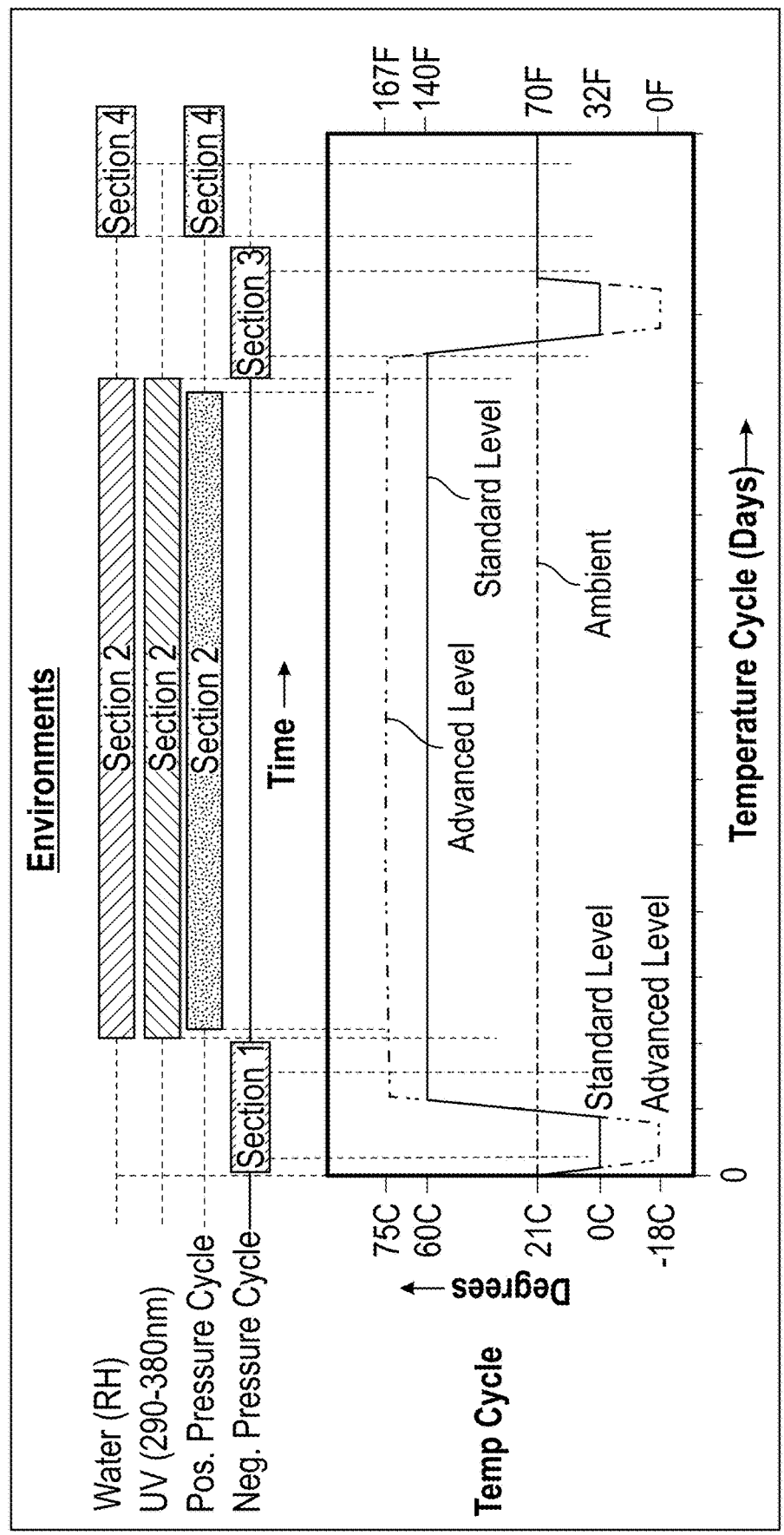
FIG. 8 is a time-chart illustrating one possible version of static and cyclical environments for testing insulating glass units.

FIG. 8 shows a time-chart illustrating one possible version of static and cyclical environments for testing insulating glass units. The time chart can optionally be provided electronically by the data acquisition and control system 500 (e.g., via a display on a computer) or in a printed report. As shown in the chart, pressure can be varied (e.g., by the air system 200) via a negative pressure cycle and a positive pressure cycle. The test sample(s) 600 can also be exposed to UV radiation in cycles (e.g., a period of time where UV light is not applied, followed by a period of time where UV light is applied). Additionally, the test sample(s) can be exposed to a humidity cycle, as shown, with a period of time with no or little humidity followed by a period of time with a higher humidity level. Temperature in the vessel can also be varied in cycles, as shown. As discussed above, the system 1000, 1000' can advantageously cycle pressure more quickly (e.g., in cycles of approximately 1 minute).

Figure 9:
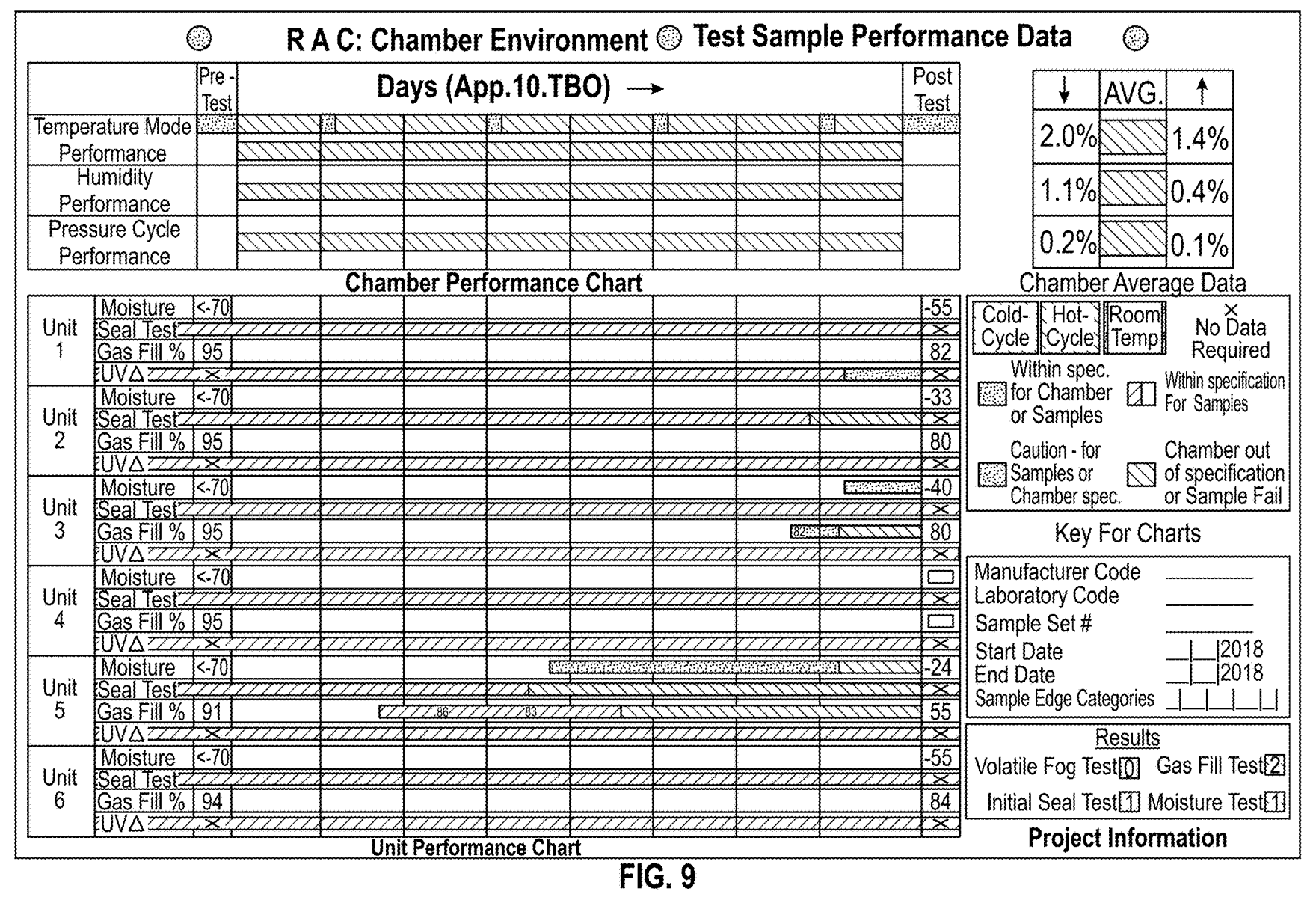

FIG. 9 is a time-chart illustrating the measured environmental conditions within the chamber 100, 100A, 100B along with the gas sealed within each of six insulating glass unit test samples, which provides data related to the durability performance of the samples' air-tight seals. The time chart can optionally be provided electronically by the data acquisition and control system 500 (e.g., via a display on a computer) or in a printed report.

Though the system 1000, 1000' and vessel 100, 100A, 100B are described above are discussed in connection with IGUs, one of skill in the art will recognize that other products can be tested. They system 1000, 1000' is particularly probative for products with air-tight seals. Manufactured components or sample products are placed in one or more sealed air chambers 100, 100A, 100B and advantageously exposed to a rapid cyclical pressure range and various static, and potentially destructive, environments. The environments would be typically harsher than those expected during the product's life-time exposure. The testing process thereby advantageously speeds up the degradation process of the sample products to evaluate their durability and quality.

In one implementation, the system 1000, 1000' and vessels 100, 100A, 100B are operable to evaluate the quality and durability of insulating glass unit (IGU) test samples. The system 1000, 1000' has one or more sealed air chambers (e.g., vessel 100, 100A, 100B) typically containing six, or more, test samples and includes a source to supply a level of incident ultraviolet radiation adjacent to the edges of at least one of the four edges of the test samples. The system 1000, 1000' also includes a compressor pump-valve system, a mechanical air exchanger system and a computer system. The compressor pump rapidly cycles the chamber's pressure from specified negative to positive values, relative to the atmospheric pressure. The air exchanger system raises and lowers temperature and moisture content of the sealed air. The included computer system, for quality assurance purposes, controls the physical environmental properties of the air in the chambers by continuously monitoring it for compliance with a specification and moving the air around the system. After completion of a prescribed test period the samples are removed from the chambers and checked by the usual ASTM methods for gas fill percentage and the air's moisture content.

In accordance with one implementation, one or all of the IGUs' gas-spaces contain a multi-channel wireless microsensor (e.g., with a powered Bluetooth wireless connection) to relay physical property data of the test samples' sealed gas, in real-time, to the device's computer storage system 500. The real-time sensors in the IGU allow the accelerated weathering system 1000, 1000' to validate the test specification for degradation rate which can be inferred to correlate to the degree of workmanship and durability. The physical properties monitored inside the test samples can include, but are not limited to, one or more of: temperature, pressure, moisture content, incident ultra-violet radiation, and argon or krypton percentage content. Combined, these properties provide real-time data to assess the condition and durability of the test sample's gas-tight seals during the testing process. The vessel 100, 100A, 100B and the test sample 600 properties are monitored by the computer system 500, and a time-graph summary of the real-time chamber environment and the real-time response of the test samples are displayed on a single page or screen for ease of evaluation (see FIGS. 8-9).

Advantageously, the invention provides an improved accelerated weathering system 1000, 1000' with a high degree of control over a full range of physical test conditions. It includes one or more sealed test chamber vessels 100, 100A, 100B and four interconnected systems: 1) an air system 200 to move the sealed air around the vessel 100, 100A, 100B and to vary the pressure in the vessels 100, 100A, 100B; 2) a cooling and dehumidification system 300 to lower the temperature and moisture content in the vessel 100, 100A, 100B; 3) a heating and humidification system 400 to increase the temperature and moisture content in the vessel 100, 100A, 100B; and 4) a computer system 500 to control the environmental conditions, collect the real-time data, edit, and present a convenient summary of the environment and the air or gas sealed in the test sample(s) 600.

Advantageously, the system 1000, 1000' exposes the test samples 600 to various stressful air environments (e.g., by moving the air into or out of the sealed vessels 100, 100A, 100B to increase or reduce the internal air pressure in the sealed vessel 100, 100A, 100B). The control is achieved by the use of pressure, temperature, and humidity sensors along with valves and electrically operated relay switches to operate: the heating coil 80 submersed in water to generate heat and humidity, a chiller 310 providing glycol to a heat exchanger 330 and to the center of the vessel 100, 100A, 100B to cool and dehumidify it.

As discussed above, the data acquisition and control system 500 provides controls to operate the mechanisms to set the conditions of the air and the UV radiation in the sealed vessels 100, 100A, 100B to a specification with prescribed tolerances. The three additional functions are: a) to collect, in real-time, data relating to the physical properties of the air in the vessel 100, 100A, 100B; b) to collect, in real-time, data relating to the physical properties of the air sealed in the insulating glass unit test samples' 600 airspace or gas-space; and c) to presents the air property data in a condensed (e.g., color-coded) time graph that displays the vessel's 100, 100A, 100B environment related to its specification and each of the test sample's physical responses. This graph presents both quality assurance information and the test samples' performance data and, if applicable, a pass/fail result.

In one implementation, one or more components of the system 1000, 1000' are assembled on a frame, improving the portability of the system. For example, the vessel 100, the exchanger system, the air and water pipes, the mechanical equipment, and the electrical and computer system components of the system 1000, 1000' can be assembled on a frame, insulated where required, and supplied by 110-volt electric power and a supply of water at a minimum of 400 kPa (40 psi). The assembled framework can then be readily moved (e.g., around a laboratory).

While certain embodiments of the inventions have been described, these embodiments have been presented by way of example only and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of the stated amount. As another example, in certain embodiments, the terms "generally parallel" and "substantially parallel" refer to a value, amount, or characteristic that departs from exactly parallel by less than or equal to 15 degrees.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during prosecution of the application, which examples are to be construed as non-exclusive.

Of course, the foregoing description is that of certain features, aspects and advantages of the present invention, to which various changes and modifications can be made without departing from the spirit and scope of the present invention. For example, though embodiments above describe a test system. Moreover, the test system need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed test system.

What is claimed is:

1. An accelerated weathering system, comprising:
one or more non-rotating air-sealed vessels, each configured to removably and simultaneously house a plurality of insulating glass unit test samples disposed circumferentially about a central axis of the one or more non-rotating air-sealed vessels;
an air flow system comprising a compressor pump-valve system and in fluid communication with a chamber in each of the one or more non-rotating air-sealed vessels that house the one or more insulating glass unit test samples, the air flow system operable to increase or decrease a pressure in the chamber;
an exchanger system in communication with the chamber and operable to increase or decrease one or both of a temperature and a humidity level of the chamber;
a plurality of UV bulbs disposed in an annular gap in each of the one or more non-rotating air-sealed vessels between the central axis and the plurality of insulating glass unit test samples, the plurality of UV bulbs being evenly distributed in the annular gap and spaced from each other about the central axis, each of the UV bulbs being supported at a top end thereof by a frame connected to a wall of the non-rotating air-sealed vessel so that each of the UV bulbs is positioned proximate opposite edges of adjacent insulating glass unit test samples and so that each of the UV bulbs is positioned closer to said opposite edges than a center of the vessel, each of the UV bulbs being operable to simultaneously expose at a least a portion of two adjacent insulating glass unit test samples to a UV light; and
a computer system operable to control the air flow system and exchanger system to vary one or more of the following parameters in the chamber: temperature, relative humidity, and pressure,
wherein each of the one or more insulating glass unit test samples is supported in a fixed orientation between a pair of brackets inside the chamber, the pair of brackets contacting a lower end of the insulating glass unit test samples.

2. An accelerated weathering device according to claim 1 wherein the pump-valve system is controlled by the computer system and is configured to operate in a transfer mode and a circulation mode.

3. An accelerated weathering device according to claim 2 wherein when operating in the transfer mode and circulation mode, both an upper and lower values of an air pressure cycle vary within a specified range relative to atmospheric pressure within a cycle time.

4. An accelerated weathering device according to claim 3 wherein sides of the said insulating glass unit test samples are arranged in the sealed air chambers in a regular polygonal shape.

5. An accelerated weathering device according to claim 4 further comprising a computer system database, wherein at least one said insulating glass unit test sample or the sealed chamber contains a micro-sensor configured to transmit real-time internal physical property data to the computer system, wherein the physical property data is stored in the computer system database.

6. An accelerated weathering device according to claim 5 wherein selected physical properties of a sealed gas in the chambers is assessed and edited by the said computer system in real-time with results presented in a systematic time-graph format.

* * * * *

UNITED STATES PATENT AND TRADEMARK OFFICE
CERTIFICATE OF CORRECTION

| | | |
|---|---|---|
| PATENT NO. | : 11,460,393 B2 | |
| APPLICATION NO. | : 16/896469 | |
| DATED | : October 4, 2022 | |
| INVENTOR(S) | : Kent | |

It is certified that error appears in the above-identified patent and that said Letters Patent is hereby corrected as shown below:

In the Claims

Column 10, Line 57 Claim 1, delete "at a" and insert -- at --.

Signed and Sealed this
Tenth Day of January, 2023

Katherine Kelly Vidal
*Director of the United States Patent and Trademark Office*